(12) United States Patent
Kohler

(10) Patent No.: US 7,651,476 B2
(45) Date of Patent: Jan. 26, 2010

(54) PROTECTIVE CLIPS

(75) Inventor: Matthew E. Kohler, East Greenville, PA (US)

(73) Assignee: B. Braun Medical Inc., Bethlehem, PA (US)

( * ) Notice: Subject to any disclaimer, the term of this patent is extended or adjusted under 35 U.S.C. 154(b) by 1017 days.

(21) Appl. No.: 10/954,041

(22) Filed: Sep. 28, 2004

(65) Prior Publication Data

US 2006/0074384 A1 Apr. 6, 2006

(51) Int. Cl.
*A61M 5/00* (2006.01)
*A61M 5/32* (2006.01)

(52) U.S. Cl. .................. 604/110; 604/198; 604/263
(58) Field of Classification Search ............... 604/110, 604/263, 158, 164, 164.08, 192–198
See application file for complete search history.

(56) References Cited

U.S. PATENT DOCUMENTS

| | | | |
|---|---|---|---|
| 4,548,658 | A | 10/1985 | Cook |
| 4,929,241 | A | 5/1990 | Kulli |
| 5,053,017 | A | 10/1991 | Chamuel |
| 5,322,517 | A | 6/1994 | Sircom et al. |
| 5,328,482 | A | 7/1994 | Sircom et al. |
| 5,882,337 | A * | 3/1999 | Bogert et al. ............. 604/110 |
| 6,117,108 | A * | 9/2000 | Woehr et al. ............. 604/110 |
| 6,287,278 | B1 | 9/2001 | Woehr et al. |
| 6,595,955 | B2 * | 7/2003 | Ferguson et al. ......... 604/110 |
| 6,616,630 | B1 | 9/2003 | Woehr et al. |
| 6,709,419 | B2 | 3/2004 | Woehr |
| 2002/0193745 | A1 | 12/2002 | Ferguson |
| 2005/0075609 | A1 * | 4/2005 | Latona ................ 604/164.08 |

OTHER PUBLICATIONS

Manan Medical Products, Inc. TipTrap™ (Commercial Art Available) (4 sheets, resubmitted with commercial product name.).
Available commercial art (5 sheets).
Patent Abstracts of Japan; entitled "Protector", Application No. 2001-006446, Publication No. 2002-210005; Date of Publication Jul. 30, 2002, Applicant Terumo Corp. , 11 pgs.
Patent Abstracts of Japan; entitled "Protector", Application No. 2002-279939, Publication No. 2004-113394, Date of Publication Apr. 15, 2004, Applicant Terumo Corp., 19 pgs.

(Continued)

*Primary Examiner*—Matthew F Desanto
(74) *Attorney, Agent, or Firm*—Klein, O'Neill & Singh, LLP

(57) ABSTRACT

Protective needle clips of the type having an arm and a body section for blocking a needle tip of a needle and for securing onto the needle are discussed herein. The body section has a free end, a fixed end, is generally arcuate, and has a resilient force capable axially expanding the body section when the free end is fixed behind a ledge to create a bias in the body section. A pair of openings on the body section is adapted to received a hypodermic needle. When the tip of the needle moves proximal of a shielding section on the protective clip, the free end disengages from the ledge and causes the body section to axially expand. The expansion changes the orientation of the openings relative to the needle to permit the openings to engage the needle.

22 Claims, 3 Drawing Sheets

OTHER PUBLICATIONS

Patent Abstracts of Japan; entitled "Protector", Application No. 2002-281982, Publication No. 2004-113523, Date of Publication Apr. 15, 2004, Applicant Terumo Corp., 16 pgs.

Patent Abstracts of Japan; entitled "Protector", Application No. 2002-281983, Publication No. 2004-113524, Date of Publication Apr. 15, 2004, Applicant Terumo Corporation, 16 pgs.

* cited by examiner

PROTECTIVE CLIPS

Protective clips are generally discussed herein for shielding needle tips of hypodermic needles to prevent accidental contact therewith with particular discussion extended to protective clips comprising a curved force generating section.

BACKGROUND

Protective needle clips are well known in the art for use in conjunction with hypodermic needles. Broadly speaking, a typical prior art protective needle clip is mounted over a hypodermic needle. The prior art protective needle clip typically has a body and at least one resilient portion, which may be inherently resilient or is caused or urged to be resilient by an exterior resilient member, such as a spring.

After an injection, the hypodermic needle is withdrawn from a body and cause to travel relative to the needle clip so that the needle clip moves from a proximal position on the needle to a distal position on the needle where the needle tip is located. When the needle clip reaches the distal end near the needle tip, the at least one resilient portion is caused to move radially inwardly over the needle tip to block the needle tip. Other mechanisms may be incorporated with the prior art needle clip to activate the resilient portion, to launch the needle clip, or to retain the needle clip on the needle.

Although prior art needle clips provide workable options for health care workers, there is a continuing need for an improved and/or alternative needle clip. Accordingly, disclosed herein are improved alternative needle clips that have a curved force generating section for biasing a different section of the clip over the needle tip of a hypodermic needle. Also disclosed are methods for using and making the same.

SUMMARY

The present invention provides for protective needle clips. More particularly, the present invention may be practiced by providing a protective clip for shielding a needle tip comprising an arm and a body section; the arm comprising a shielding section and a ledge and the body section comprising a proximal opening, a distal opening, and a free end. In one exemplary embodiment, the free end is in contact with the ledge, the body section comprises an arch and a resilient force capable of axially expanding the body section, and the proximal and distal openings are in alignment for receiving a needle.

The present invention may also be practiced by providing a protective clip for shielding a needle tip comprising an arm and a body section comprising a proximal opening, a distal opening, and a free end. The body section being curved and comprising an arch, the free end being in contact with a ledge extending from an end of the arm, and wherein the proximal and distal openings are configured to receive a needle.

In still yet another aspect of the present invention, there is provided a protective clip for shielding a needle tip comprising an arm and a body section; the arm comprising a shielding section and a ledge and the body section comprising a proximal opening, a distal opening, and a free end; the proximal and distal openings being in alignment and having a needle passing therethrough; the needle being in contact with the shielding section to bias the arm radially outwardly, and the free end of the body section being in contact with the ledge.

BRIEF DESCRIPTION OF THE DRAWINGS

These and other features, aspects and advantages of the present invention will be more fully understood when considered with respect to the following detailed description, appended claims and accompanying drawings, wherein:

DETAILED DESCRIPTION

The detailed description set forth below in connection with the appended drawings is intended as a description of the presently preferred protective needle clip embodiments provided in accordance with aspects of the present invention and is not intended to represent the only forms in which the present invention may be constructed or utilized. The description sets forth the features and the steps for constructing and using the protective needle clips of the present invention in connection with the illustrated embodiments. It is to be understood, however, that the same or equivalent functions and structures may be accomplished by different embodiments that are also intended to be encompassed within the spirit and scope of the invention. Also, as denoted elsewhere herein, like element numbers are intended to indicate like or similar elements or features.

Figure 1:
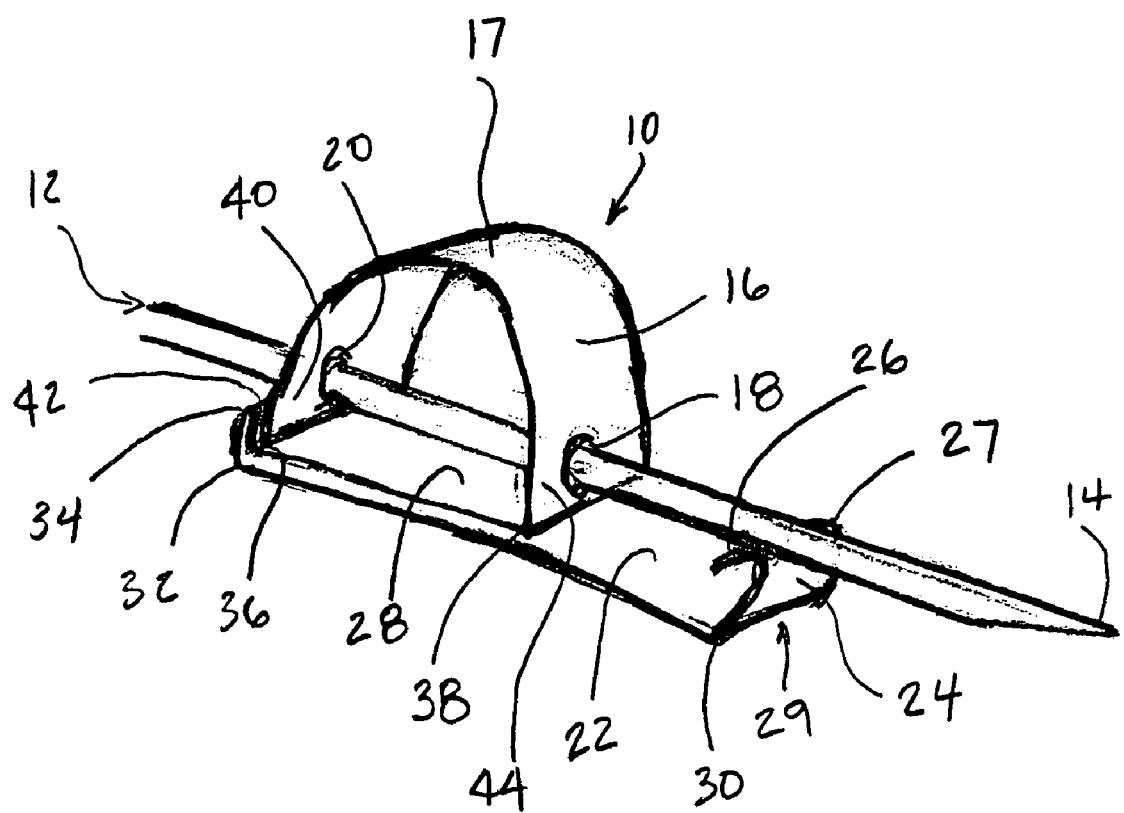
FIG. 1 is a semi-schematic perspective view of a protective clip provided in accordance with aspects of the present invention mounted on a needle.

Referring to FIG. 1, a semi-schematic perspective view of a protective clip 10 provided in accordance with aspects of the present is shown mounted on a hypodermic needle 12. As shown, the clip 10 is in a pre-activated or first position on the needle 12, which is a position before the clip shields the needle tip 14.

In one exemplary embodiment, the clip 10 comprises a body section 16 comprising a distal opening 18 and a proximal opening 20. The body section 16 is curved and comprises an arch 17. The clip 10 also comprises an elongated arm 22, a finger 24, a tip 26, and a curve 27. The finger 24, the tip 26, and the curve 27 are herein occasionally referred to collectively as the shielding section 29. In one exemplary embodiment, a second elongated arm 28 is incorporated. The second elongated arm 28 connects the curved body section 16 to the first elongated arm 22. Although shown parallel with one another, the first elongated arm 22 and the second elongated arm 28 may be non-parallel when in the position shown.

In one exemplary embodiment, the clip 10 shown in FIG. 1 is made by stamping an elongated rectangular strip of a thin planar sheet, such as a stainless steel sheet, stamping two openings on said stamped strip, and folding, rolling, or bending the stamped sheet into the configuration shown. Thus, in one exemplary embodiment, the clip 10 is integrally formed by making a first roll or bend at the first curve 27, a second bend at the second curve 30, a third bend at the third curve 32, a fourth bend at the fourth curve 34, a fifth bend at the fifth curve 36, a sixth bend at a sixth curve 38, and a seventh bend to form the curved body section 16 of the clip 10. In another exemplary embodiment, the tip 26 and the finger 24 may also be bent to form a curved tip and a curved finger. Note that while the curved sequence of the various corners is described to more readily identify the corners, the bent corners may not necessarily be bent or produced in the sequence described. In other words, in an alternative embodiment, the corners can be produced in a different sequence. In another alternative embodiment, the first curve 27 and the tip 26 may be omitted. In another exemplary embodiment, the curved body section 16 and the elongated arm 22 may be made by combining two or more sub-components made from a metal or a combination of a metal and a thermoplastic. In another embodiment, the stamped strip for forming the clip may incorporate curves and/or notches for creating different contours and curvatures.

The clip 10 is placed in the ready, pre-activated, or first position shown in FIG. 1 by pushing the free end 40 of the curved body section 16 behind a wedge or ledge 42 formed by the third curve 32, fourth curve 34, and fifth curve 36. When the free end 40 is not positioned behind the wedge 42, the length of the curved body section 16 measured between the free end 40 and the fixed end 44 is longer than the length of the second elongated arm 28, which extends between the tip of the fixed end 44 and the wedge 42. Accordingly, when the free end 40 is secured behind the wedge 42, the curved body section 16 is compressed and resembles a loaded spring having a spring force. The force can vary by forming the clip from material of different stiffness, using a thicker rectangular strip, using a wider rectangular strip, adding additional curves within the arch 17 of the curved body section 16 to create multiple coiled sections, providing a large arch, and bending the curved body section 16 a greater amount. In one exemplary embodiment, the ledge 42 comprises a generally flat section comprising a height extending above the second elongated arm 28 a sufficient amount to retain the curved body section 16 in the ready position. However, the height of the ledge 42 should not be so great so as to obstruct the free end 40 and prevents the free end from separating from the ledge when the clip is activated or prevent the needle 12 from passing through the two openings 18, 20.

In one exemplary embodiment, when the clip 10 is placed in the ready position, the distal opening 18 and the proximal opening 20, which, of course, have diameters larger than the diameter of the needle 12, are aligned so that the needle 12 may pass through both openings. To set the clip 10 further proximal on the needle 12, i.e., further away from the tip 14, the finger 24 is pushed downwardly to provide clearance for the needle, which causes the first elongated arm 22 to flex radially outwardly from the axis defined by the needle 12. Say differently, when the clip 10 is in the ready position, the point on the top of the first curve 27 is higher than the highest point on the distal opening 18. Thus, to provide clearance for the needle 12, the finger 24 is biased downwardly, which requires the first elongated arm 22 to flex. By flexing the elongated arm 22, the free end 40 is also secured to the wedge 42.

Figure 2:
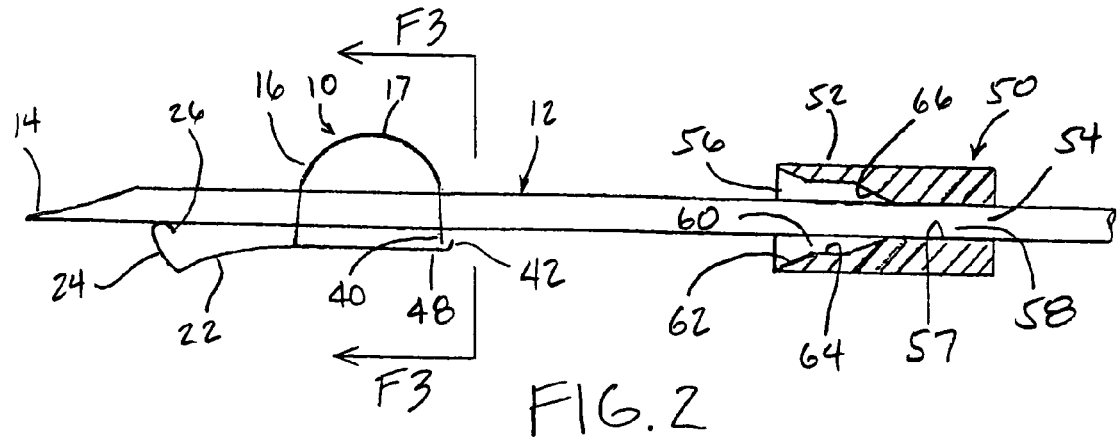
FIG. 2 is a semi-schematic partial cross-sectional side view of the clip and needle of FIG. 1 with a pusher for pushing the clip.

Referring now to FIG. 2, a semi-schematic side view of the clip 10 and the needle 12 of FIG. 1 is shown from a reversed angle. For simplicity, the clip 10 is shown with the second elongated arm 28 superimposed with the first elongated arm 22. As previously discussed, the elongated arm 22 is flexed to accommodate the needle 12. The flexing creates an upward force at the proximal end 48 of the elongated arm near the wedge 42.

A pusher 50 comprising a generally cylindrical body 52 comprising a proximal opening 54, a distal opening 56, and an axial bore 58 connecting the proximal opening and the distal opening is mounted on the needle 12 proximally of the clip 10. In one exemplary embodiment, the pusher 50 is a means by which the clip 10 is moved from a proximal position on the needle 12 to a distal position on the needle to activate the clip 10 to then shield the needle tip 14 from accidental contact therewith. However, the clip 10 may be moved by a user's finger, a spring, or any other means capable of moving the clip from a proximal position on the needle 12 to a distal position on the needle. Accordingly, the pusher 50 is an optional device for moving the clip 10.

In one exemplary embodiment, the pusher 50 is molded from a hard thermoplastic, which can be any thermoplastic or plastic blend currently available on the market. Preferably, the thermoplastic is polypropylene. The pusher 50 may have an opaque appearance, a semi-opaque appearance, one or more colors, and/or texture for aesthetic appeal. In one exemplary embodiment, the distal opening 54 and the proximal section 57 of the passage 58 comprise a diameter measured approximately 1 to 10 mils larger than the diameter of the needle 12. Preferably, the diameter is measured approximately 1-7 mils larger than the diameter of the needle and more preferably between 1-3 mils larger than the diameter of the needle 12. In one exemplary embodiment, the distal opening 56 comprises a diameter measured less than the height of the clip 10 measured from the elongated arm 22 to the peak of the arch 17 of the curved body section 16. Preferably, the distal opening 56, more specifically the perimeter of the opening 56, is such that when the pusher 50 is pushed against the clip 10, the perimeter of the opening 56 contacts the arch 17 of the curved body section but not the wedge 42. This permits the portion of the arm 22 adjacent the wedge 42 to rotate radially outwardly away from the axis of the needle 12.

In one exemplary embodiment, the distal passage section 60 of the passage 58 comprises a plurality of different diameter sections. For example, the distal section 60 may have a tapered entrance section 62, a round mid-section 64, and a tapered rear section 66 that intersects the proximal passage section 57. In another embodiment, the tapered entrance section 62 extends proximally and intersects the proximal passage section 57. As further discussed below, the tapered entrance section 62 should incorporate an angle such that the wedge 42 on the clip 10 is able to rotate radially outwardly without being delimited by the distal passage section 60.

Figure 3:
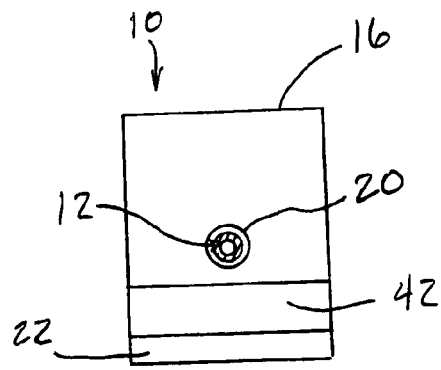
FIG. 3 is a semi-schematic end view of the clip of FIG. 2 taken along line F3-F3.

Referring now to FIG. 3, an end-view of the clip 10 taken along line F3-F3 of FIG. 2 is shown. In the ready position, both the distal 18 and proximal 20 openings, with only the proximal opening 20 shown in FIG. 3, have a generally circular projection. As is readily apparent to a person of ordinary skill in the art, when any circular opening is viewed directly in an upright position by a viewer standing upright, the circular opening has a circular projection. In contrast, when the same circular opening is tilted away from the viewer, or towards the viewer, the opening has a generally oval or ellipse projection with the narrow portion of the oval being aligned along the vertical direction and the longer portion of the oval being aligned along the horizontal direction. Hence, since FIG. 3 is an end view of the clip 10 taken along line F3-F3 of FIG. 2 with the clip being in the ready position, the needle 12 and the proximal opening 20 have a generally circular projection. For simplicity, FIG. 2 shows the distal opening 20 being generally circular although it is recognized that since the curved body section 16 is tilted slightly forward at the opening 20 due to the curvature of the arch 17, the projection is not a true circle.

Still referring to FIG. 3, in one exemplary embodiment, the proximal opening 20 of the clip 10 has a diameter of about 1-10 mils larger than the diameter of the needle 12 with the range of 1-3 mils being more preferred. However the proximal opening 20 may have a different diameter range provided the spring force generated by the curved body portion 16, as further discussed below, is sufficiently strong to permit the opening 20 to grip the needle 12 when the opening 20 is tilted forward to take on an oval projection. In one exemplary embodiment, the distal opening 18 has a same diameter range as the diameter range of the proximal opening 20.

Figure 4:
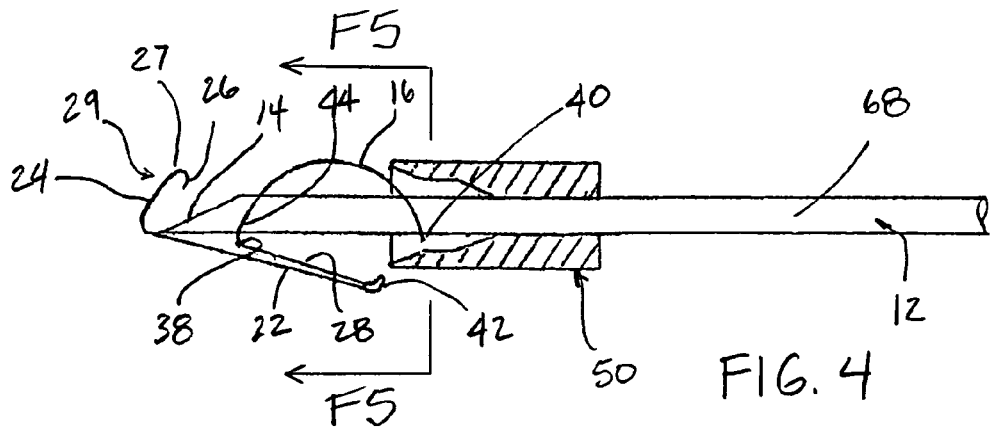
FIG. 4 is a semi-schematic partial cross-section side view of the clip and pusher of FIG. 2 with the clip in an activated position.

Referring now to FIG. 4, a semi-schematic side view of the needle 12 and the clip 10 of FIG. 2 is shown with the clip in the activated or second position. The clip 10 is activated by pushing the clip distally towards the needle tip 14. If a pusher 50 is incorporated, the clip 10 is pushed by the pusher 50. If there is no pusher, then the clip 10 may be pushed by a user's finger. As the shielding section 29 of the clip moves distally of the needle tip 14, the bias on the elongated arm 22 by the needle is released and the elongated arm 22 moves radially inwardly which then moves the shielding section 29 over the needle tip 14 to shield the needle tip.

In one exemplary embodiment, when the shielding section 29 moves distally of the needle tip 14, the bias on the elongated member 22 (See, e.g., FIG. 2) is released and the elongated member 22 springs radially inwardly in returning to its normal configuration. In springing back to its normal configuration, the force and the momentum of the elongated member 22 separates the wedge 42 from the free end 40 of the curved body section 16. The separation of the free end 40 from the wedge 42 in turn releases the constraint on the curved body portion 16 and permits the curved body portion to axially expand along the length of the needle shaft 68. This in turn causes the distal opening 18 and the proximal opening 20 to tilt further from vertical over the needle 12. Consequently, each opening contacts the needle 12 along an upper portion and a lower portion of the opening, i.e., contact the needle at the narrow portion of the oval projection to grip the needle 12. The clip 10 is now activated to shield the needle tip 14 of the needle 12.

In one exemplary embodiment, the shape and size of the arch 17, the material of the clip, and the size of the proximal and distal openings 18, 20 are such that sufficient gripping force is generated at each opening to permit the two openings to grip the needle 12 when the clip is activated. The openings 18, 20 should have a grip that is sufficient to maintain the clip 10 at the end of the needle adjacent the needle tip during normal use following an injection.

Figure 5:
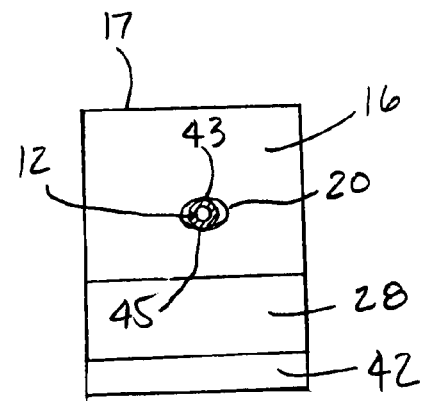
FIG. 5 is a semi-schematic end view of the clip of FIG. 4 taken along line F5-F5.

FIG. 5 is a semi-schematic end view of the clip 10 and the needle 12 taken along line F5-F5 of FIG. 4, shown without the pusher 50 for clarity. In the view shown, the curved body portion 16 expands over the needle 12 and the portion of the arch 17 at the distal opening 20 tilts forward in the direction of the needle tip. Due to the tilt, the distal opening 20 takes on an oval projection and contacts the needle 12 along the top 43 and the bottom 45 of the needle, with top and the bottom being corresponding to the top and the bottom of the page. The left side and the right side of the needle 12 remain spaced apart from the left side and the right side of the distal opening 20, with the left side and the right side being corresponding to the left side and right side of the page.

Figure 6:
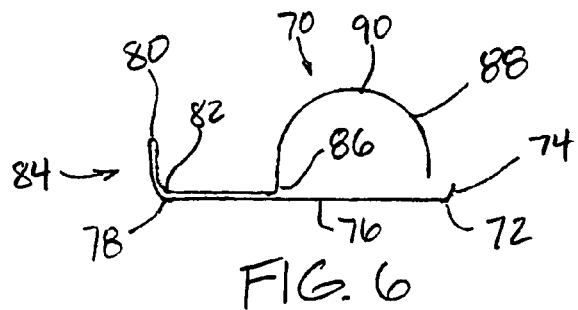
FIG. 6 is a semi-schematic side view of an alternative clip provided in accordance with aspects of the present invention.

Referring now to FIG. 6, a semi-schematic side view of an alternative protective clip 70 provided in accordance with aspects of the present invention is shown. In the present embodiment, the clip 70 is formed by taking a stamped metal strip and rolling the strip at a first curve 72 to form a wedge 74. Then rolling the strip at a second curve 78, third curve 80, and fourth curve 82 to form a shielding section 84, and rolling the strip at a fifth curve 86. Finally, rolling a large arch 90 to form the curved body portion 88. Although not shown, a proximal opening and a distal opening are formed on the curved body portion 88 to receive a needle, similar to the proximal and distal openings 18, 20 on the clip 10 of FIG. 1. An elongated arm 76 is located between the first curve 72 and the second curve 78.

Figure 7:
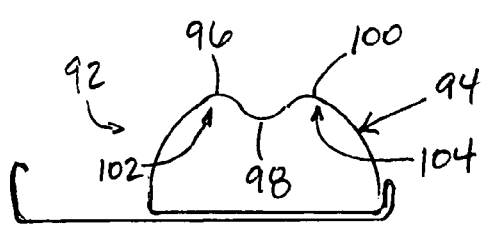
FIG. 7 is a semi-schematic side view of another alternative clip provided in accordance with aspects of the present invention.

FIG. 7 is a semi-schematic side view of another alternative protective clip 92 provided in accordance with aspects of the present invention. The alternative clip 92 is similar to the clip 10 of FIG. 1 in that it incorporates several rolled curves from a single metal strip. However, several additional rolled curves are incorporated in the curved body section 94 to provide a curved body section with added resilient coiled affects. In one exemplary embodiment, a first body curve 96, a second body curve 98, and a third body curve 100 are incorporated to produce two resilient coils 102, 104. When the clip 92 is mounted over a needle and activated to shield the needle tip, the resilient coils 102, 104 provide the curved body section 94 with added biasing force for a stronger gripping force on the needle by the distal opening and proximal opening (not shown) than a comparable clip with a single resilient coil.

Figure 8:
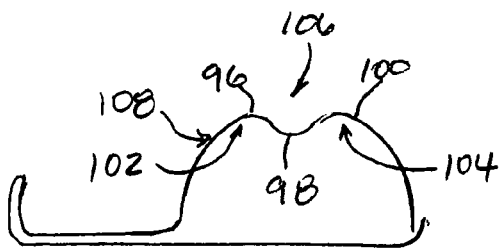
FIG. 8 is a semi-schematic side view of yet another alternative clip provided in accordance with aspects of the present invention.

FIG. 8 is a semi-schematic side view of yet another alternative protective clip 106 provided in accordance with aspects of the present invention. The clip is similar to the clip 70 of FIG. 6 in that it incorporates a several rolled curves made from a stamped metal strip. Like the clip 92 of FIG. 7, the present alternative clip 106 incorporates a first body curve 96, a second body curve 98, and a third body curve 100 on its curved body section 108 to produce two resilient coils 102, 104. The present clip 106 is able to produce a stronger gripping force on the needle at the distal opening and the proximal opening (not shown) than a comparable clip with a single resilient coil.

Figure 9:
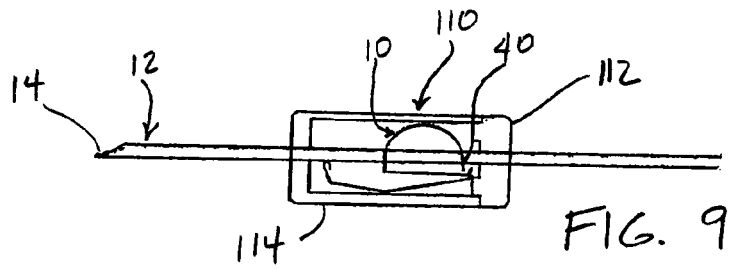
FIG. 9 is a semi-schematic cross-sectional side view of the clip and needle of FIG. 1 with the clip positioned inside a pusher enclosure.

FIG. 9 is a semi-schematic partial cross-sectional side view of the clip 10 of FIG. 1 mounted on a needle 12 and located inside a pusher enclosure 110. In one exemplary embodiment, the pusher enclosure 110 surrounds the clip and is configured to deter or limit after activation contact with the clip 10 by a user. The pusher enclosure 110 comprises a base 112 and an elongated body section 114 made from either a semi-hard or a hard thermoplastic. Preferably, the thermoplastic is transparent so that the clip 10 may be viewed by a user through the enclosure 110. Obviously, the thermoplastic may be opaque or semi-opaque. In one exemplary embodiment, the base 112 comprises a proximal opening for receiving the needle 12 and is formed with either male or female detents. In one exemplary embodiment, the elongated body section 114 is generally cylindrical in shape, incorporates a distal opening for receiving the needle, and incorporates corresponding male or female detents for engaging the base 112.

The pusher enclosure 110 and the clip 10 may be mounted over the needle 12 by first sliding the base 112 onto the needle 12 then follow by the clip 10. The elongated body section 114 is then slid on the needle 12 and over the clip 10 and is caused to engage the base 112 by forcing the detents on the base on the elongated body section 114 to mate. The enclosure 110 and the clip 10 are then pushed proximally along the needle 12 to a desired final position, which in one exemplary embodiment includes pushing the housing and the clip proximally until the base 112 contacts a needle hub.

To activate the clip 10 to shield the needle tip 14 from accidental contact therewith, the pusher enclosure 110 is grasped and pushed distally over the needle 12. Once the shielding section 29 moves distal of the needle tip 14, the elongated arm 22 rotates radially to move the shielding section 29 over the needle tip 14, as previously discussed. Subsequently, the proximal and distal openings (not shown) on the curved body section 16 grip the needle 12 to prevent the clip 10 from dislodging from the end of the needle, also as previously discussed.

Figure 10:
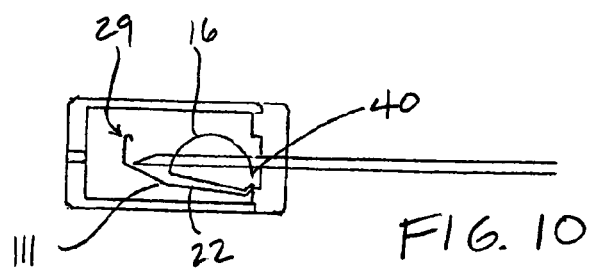
FIG. 10 is a semi-schematic cross-sectional side view of the clip, needle, and pusher enclosure of FIG. 9 with the clip in an activated position.

As is readily apparent from FIG. 10, the free end 40 of the clip 10 is covered or enclosed by the enclosure 110. Thus, the free end 40 cannot be pushed or otherwise tempered with to cause the proximal and distal openings to move from their oval projection to their circular projection and lose their grip on the needle 12. In one exemplary embodiment, the elongated arm 22 incorporates a bent 111 for facilitating radial movement of the shielding section 29 over the needle tip. Note that while the clip 10 of FIG. 1 is shown located inside the pusher enclosure 110, any of the various alternative clips described elsewhere herein may be used in combination with the pusher enclosure.

The various clips described elsewhere herein may be used to protect the needle tip of a safety spinal needle, a Huber needle, or any needle where a needle tip is desired to be shielded following an injection. For use with a catheter assembly where one of the various clips described elsewhere herein is to be mounted inside a catheter hub, means for coupling the clip with the interior cavity of the catheter hub should be incorporated. As is well known in the art, following an injection using a catheter assembly, the catheter tube is left in place while the needle and needle hub are withdrawn from the catheter tube and catheter hub. Thus, for a clip to shield the needle tip of a catheter assembly following an injection, the clip must first be positioned inside the catheter hub and move relative to the needle when the needle is withdrawn from the catheter tube until the needle tip moves near the clip, at which point the clip must disengage from the catheter hub, shield the needle tip, and move with the needle relative to the catheter hub. Further discussion regarding how a clip operates when mounted inside a catheter assembly is described in U.S. Pat. No. 6,616,630, the contents of which are expressly incorporated herein by reference.

In one exemplary embodiment, the means for mounting the clip described elsewhere herein with a catheter hub may include a bump, a projection, a ring, or a groove formed inside the interior cavity of the catheter hub. The highest point on the curve body section of the clip may then engage the bump, projection, ring, or groove to engage the clip to the catheter hub and to thereby permit the clip to move relative to the needle when the needle is withdrawn from the catheter tube. As the needle tip moves proximally of the shielding section of the clip, the elongated arm rotates radially, the curved body section expands axially and the highest point on the curve body section separates from the bump, projection, ring, or groove to then separate the clip from the catheter hub. As the curved body section expands, the proximal and distal openings grip the needle to cause the clip to attach to the needle and move with the needle relative to the catheter hub.

In another exemplary embodiment, the clips discussed elsewhere herein may incorporate retaining wings for use with a catheter assembly. Retaining wings are described extensively in Ser. No. 10/677,810, filed Oct. 1, 2003, the contents of which are expressly incorporated herein by reference. The retaining wings may be formed on the curved body section of the various clips for engaging the bump, projection, ring, or groove located inside the catheter hub. When incorporated, a pair of retaining wings may be positioned either adjacent the free end or the fixed end of the curved body section.

Although the preferred embodiments of the invention have been described with some specificity, the description and drawings set forth herein are not intended to be delimiting, and persons of ordinary skill in the art will understand that various modifications may be made to the embodiments discussed without departing from the scope of the invention, and all such changes and modifications are intended to be encompassed within the appended claims. Various changes to the needle clip comprising a radially moving arm and an axially expanding curved body section when transitioning between a ready position and an activated position may be made without deviating from the spirit and scope of the present invention. For example, the dimensions of the protective clip can vary depending on the particular hypodermic needle assembly used with the protective clip, the material selection can vary, the arc of the various curves can vary, and the protective clip can be made by assembling or bonding different components together instead of from a unitary construction. Still other changes may include using a resilient spring to advance the protective clip towards the needle tip to shield the needle tip, wedging the spring clip inside a catheter hub to be moved by the catheter hub towards the needle tip, and wedging the spring clip inside a collar of a Huber needle to be moved by the collar towards the needle tip of the Huber needle. Accordingly, many alterations and modifications may be made by those having ordinary skill in the art without deviating from the spirit and scope of the invention.

What is claimed is:

1. A protective clip for shielding a needle tip comprising:
an arm comprising a shielding section and a ledge; and
a body section comprising a proximal opening, a distal opening, a free end and a fixed distal end not axially movable relative to the arm, wherein the free end abuts the ledge of the arm to form a curved force generating section configured for axially expanding the body section when activated, and the proximal and distal openings are in alignment and receiving a needle defining a needle axis and having a needle tip;
wherein the shielding section of the arm is moveable from a first position where the shielding section is biased toward the needle axis to a second position where the bias on the arm is released to allow the shielding section to move radially toward the needle axis and distally of the needle tip;
wherein the free end is separable from the ledge of the arm when the shielding section moves distally of the needle tip.

2. The protective clip of claim 1, further comprising a pusher for pushing the protective clip distally on the needle.

3. The protective clip of claim 2, wherein the pusher comprises an internal passage comprising at least two different diameters.

4. The protective clip of claim 1, wherein the body section comprises a plurality of body curves.

5. The protective clip of claim 1, wherein the arm and the body section are integrally formed from a stainless steel sheet.

6. The protective clip of claim 1, wherein the shielding section comprises a finger and a tip.

7. The protective clip of claim 1, wherein the free end abuts both the ledge of the arm and a second elongated arm.

8. The protective clip of claim 1, wherein the body section axially expands along the axis of the needle when activated.

9. The protective clip of claim 1, wherein the ledge is located at a proximal end of the arm.

10. The protective clip of claim 1, wherein the fixed end of the body section is loser to the shielding section than the free end is to the shielding section.

11. A protective clip for shielding a need tip of a needle comprising:
   an arm including a shielding section extending from a first end of the arm;
   a body section including a proximal opening, a distal opening, a free end, a curved force generating section and a fixed end at the body section's distal most end; and
   a ledge extending from a second end of the arm opposite the shielding section; wherein the free end is in contact with the ledge to create an axial bias on the curved force generating section of the body section;
   wherein the shielding section is moveable from a first position where the shielding section is biased against a side of the needle and the curved force generating section is substantially unexpanded to a second position where the bias on the arm is released to allow the arm to move toward the central axis of the needle and cause the shielding section to move across the central axis of the needle to cover the needle tip of the needle and where the curved force generating section is expanded axially along the needle to cause the proximal opening and distal opening to grip the needle to substantially prevent the needle from moving axially relative to the body section; and
   wherein the free end separates from the ledge when the shielding section moves from the first position to the second position.

12. The protective clip of claim 11, further comprising a pusher for pushing the protective clip distally on the needle.

13. The protective clip of claim 12, wherein the pusher comprises an internal passage comprising at least two different diameters.

14. The protective clip of claim 11, wherein the body section comprises a plurality of body curves.

15. The protective clip of claim 11, wherein the arm and the body section are integrally formed from a stainless steel strip.

16. The protective clip of claim 11, wherein the free end contacts both the ledge of the arm and a second elongated arm.

17. The protective clip of claim 11, wherein the fixed end of the body section is closer to the shielding section than the free end is to the shielding section.

18. A protective clip for shielding a needle tip comprising:
   first arm comprising a shielding section and a ledge formed;
   a body section including a proximal opening, a distal opening, and a free end; the proximal and distal openings being in alignment and receving a needle passing therethrough, the needle defining a central axis and having a needle tip;
   wherein the shielding section is moveable from a non-activated position, where the needle is in contact with the shielding sectin to bias the first arm radially outwardly and the free end of the body section is in contact with the ledge, and an activated position, where the bias on the first arm is released to allow the shielding section to move radial inwardly and over the needle tip to substantially enclose the needle tip and the free end of the body section is moved radially outwardly to be free from contact with the ledge, and
   wherein a second arm is attached to the body section and comprise a surface portion parallel to a surface portion of the first arm, the first arm being positioned subjacent the second arm.

19. The protective clip of claim 18, wherein the first arm, the second arm and the body section are formed from a single stainless steel strip.

20. The protective clip of claim 18, wherein the first arm is attached and the second arm are connected to the ledge.

21. The protective clip of claim 18, wherein the ledge is located between the first arm and the second arm.

22. The protective clip of claim 18, wherein the first arm contacts the second arm in the non-activated position.

* * * * *